(12) United States Patent
Queisser et al.

(10) Patent No.: US 6,667,386 B1
(45) Date of Patent: Dec. 23, 2003

(54) WATER-SOLUBLE TRANSITION METAL COMPLEXES

(75) Inventors: Joachim Queisser, Mannheim (DE); Michael Slany, Kirchheim (DE); Michael Geprägs, Lambsheim (DE); Ekkehard Lindner, Tübingen (DE); Markus Schmid, Pfullingen (DE); Joachim Wald, Albstadt-Ebingen (DE); Peter Wegner, Tübingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/719,813

(22) PCT Filed: Jun. 22, 1999

(86) PCT No.: PCT/EP99/04312

§ 371 (c)(1),
(2), (4) Date: Dec. 18, 2000

(87) PCT Pub. No.: WO00/01708

PCT Pub. Date: Jan. 13, 2000

(30) Foreign Application Priority Data

Jul. 2, 1998 (DE) ........................................ 198 29 519

(51) Int. Cl.$^7$ .............................................. C08G 67/02
(52) U.S. Cl. ....................... 528/392; 526/142; 526/126; 526/172
(58) Field of Search ................................. 556/138, 136, 556/110, 118, 18, 16, 21; 528/392

(56) References Cited

U.S. PATENT DOCUMENTS

| | | | | |
|---|---|---|---|---|
| 5,175,244 A | * | 12/1992 | Budzelaar et al. | 528/392 |
| 5,247,065 A | | 9/1993 | van Doorn et al. | |
| 5,352,767 A | * | 10/1994 | Chien | 528/392 |
| 5,369,073 A | * | 11/1994 | Sommazzi et al. | 502/162 |
| 5,488,096 A | * | 1/1996 | Drent et al. | 528/392 |
| 5,506,338 A | * | 4/1996 | Hanna et al. | 528/392 |
| 5,521,281 A | * | 5/1996 | Sen et al. | 528/392 |
| 5,631,345 A | * | 5/1997 | Takaya et al. | 528/392 |
| 5,654,250 A | * | 8/1997 | Van Der Veer et al. | 502/162 |
| 5,670,610 A | * | 9/1997 | Somazzi et al. | 528/392 |
| 5,688,909 A | * | 11/1997 | Drent et al. | 528/392 |
| 5,952,456 A | * | 9/1999 | Bradford et al. | 528/392 |
| 6,541,564 B2 | * | 4/2003 | Schmid et al. | 524/801 |

FOREIGN PATENT DOCUMENTS

| | | | |
|---|---|---|---|
| EP | 121 965 | 10/1984 | |
| EP | 0 280 374 A2 | * 8/1988 | ........... C08G/67/02 |
| EP | 0 296 687 A2 | * 12/1988 | ........... C08G/67/02 |
| EP | 305 011 | 3/1989 | |
| EP | 428 228 | 5/1991 | |
| EP | 460 743 | 12/1991 | |
| EP | 485 035 | 5/1992 | |
| EP | 590 942 | 4/1994 | |
| EP | 702 045 | 3/1996 | |
| EP | 800 852 | 10/1997 | |
| EP | 0 800 852 A2 | * 10/1997 | ........... B01D/53/14 |
| WO | 98/22482 | 5/1998 | |
| WO | 98/25939 | 6/1998 | |

OTHER PUBLICATIONS

Verspui, G.; Schanssema, F.; Sheldon, R. A. Angew. Chem., Int. Ed. Engl. 2000, 39, 804–806.*
Lindner, E.; Schmid, M.; Wald, J.; Queisser, J. A.; Geprägs, M.; Wegner, P.; Nachtigal, C. J. Organomet. Chem. 2000, 602, 173–187.*
Baxley et al. Inog. Chem. 1996, 35, 6688.*
Baxley et al. J. Mol. Catal. 1997, 116, 191.*
Verspui et al. Chem. Commun. 1998, 401.*
Jiang et al. Macromolecules 1994, 27, 7215.*
Bartik et al. Inorg. Chem. 1994, 33, 164.*
Hamed et al. Organometallics 1998, 17, 5184.*
Chen et al. Polyhedron 1998, 17, 2271.*
Chem.Rev.1996,96,663–681, Drent et al.
Mac.1994,27,7215–7216, Jiang et al.
Chem. Commun., 1998 401–402, Verspui et al.
Angew.Chem.Int.Ed.Engl.1995,34,No.7,Herrmann et al.811–813.
Baxley et al.,J.Mol. Cat. Chem.116(1997) 191–198.
Inorg.Chem.1996, 35, 6688–6693, Baxley et al.

\* cited by examiner

*Primary Examiner*—David W. Wu
*Assistant Examiner*—Rip A. Lee
(74) *Attorney, Agent, or Firm*—Keil & Weinkauf

(57) ABSTRACT

Water-soluble transition metal complexes of the formula (I)

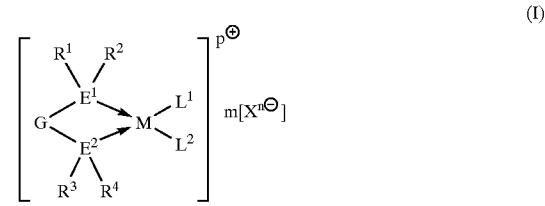

(I)

where $R^1$ to $R^4$ are linear or branched $C_2$- to $C_{28}$-alkyl, $C_3$- to $C_{14}$-cycloalkyl or alkylaryl where the alkyl moiety is of 1 to 28 carbon atoms and the aryl moiety is of 6 to 15 carbon atoms, each of which is substituted by at least one polar protic or ionic functional group based on nonmetallic elements of groups IVA to VIA of the Periodic Table of Elements.

4 Claims, No Drawings

WATER-SOLUBLE TRANSITION METAL COMPLEXES

The present invention relates to water-soluble transition metal complexes of the formula (I)

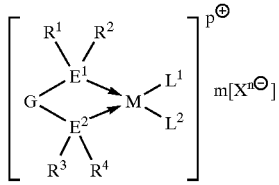

where

G is $-(CR^b{}_2)_r-$, $-(CR^b{}_2)_s-Si(R_a)_2-(CR^b{}_2)_t-$, $-A'-O-B'-$ or $-A'-Z(R^5)-B'-$, $R^5$ is hydrogen or is $C_1$- to $C_{28}$-alkyl, $C_3$- to $C_{14}$-cycloalkyl, $C_6$- to $C_{15}$-aryl, alkylaryl where the alkyl radical is of 1 to 20 carbon atoms and the aryl radical is of 6 to 15 carbon atoms, each of which is unsubstituted or substituted by functional groups based on elements of groups IVA, VA, VIA or VIIA of the Periodic Table of the Elements, or is $N(R^b)_2$, $-Si(R^c)_3$ or a radical of the formula (II)

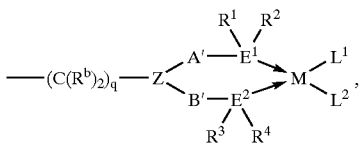

where q is an integer from 0 to 20 and the further substituents in (II) have the same meanings as in (I), A' and B' are each $-(CR^b{}_2)_{r'}-$ or $-(CR^b{}_2)_s-Si(R^a)_2-(CR^b{}_2)_t-$ or $-N(R^b)-$, an r'-, s- or t-atom component of a ring system or, together with Z, an (r'+1)-, (s+1)- or (t+1)-atom component of a heterocyclic structure, $R^a$, independently of one another, are each $C_1$- to $C_{20}$-alkyl, $C_3$- to $C_{10}$-cycloalkyl, $C_6$- to $C_{15}$-aryl or alkylaryl where the alkyl moiety is of 1 to 10 carbon atoms and the aryl moiety is of 6 to 15 carbon atoms, $R^b$ is the same as $R^a$, or hydrogen or $Si(R^c)_3$, $R^c$ is $C_1$- to $C_{20}$-alkyl, $C_3$- to $C_{10}$-cycloalkyl, $C_6$- to $C_{15}$-aryl or alkylaryl where the alkyl moiety is of 1 to 10 carbon atoms and the aryl moiety is of 6 to 15 carbon atoms, r is 1, 2, 3 or 4, r is 1 or 2, s and t are each 0, 1 or 2, where $1 \leq s+t \leq 3$, z is a nonmetallic element from group VA of the Periodic Table of Elements, M is a metal selected from the groups VIIIB, IB or IIB of the Periodic Table of Elements, $E^1$ and $E^2$ are each a nonmetallic element from group VA of the Periodic Table of Elements, $R^1$ to $R^4$ are each linear or branched $C_2$- to $C_{28}$-alkyl, $C_3$- to $C_{14}$-cycloalkyl or alkylaryl where the alkyl moiety is of 1 to 28 carbon atoms and the aryl moiety is of 6 to 15 carbon atoms, each of which is substituted by at least one polar protic or ionic functional group based on nonmetallic elements of groups IVA to VIA of the Periodic Table of Elements, $L^1$ and $L^2$ are formally charged or neutral ligands, X are formally monovalent or polyvalent anions, p is 0, 1, 2, 3 or 4, m and n are each 0, 1, 2, 3 or 4 and p = m×n.

The present invention furthermore relates to the use of these metal complexes for the preparation of linear, alternating copolymers of carbon monoxide and α-olefinically unsaturated compounds. The present invention also relates to water-soluble chelate ligands, a process for the preparation of these chelate ligands and their use for the preparation of water-soluble transition metal complexes.

Transition metal-catalyzed processes for the preparation of linear, alternating copolymers of carbon monoxide and α-olefinically unsaturated compounds, also referred to as carbon monoxide copolymers or polyketones for short, are known. For example, in EP-A 0 121 965 a cis-palladium complex chelated with bidentate phosphine ligands, [Pd(Ph$_2$P(CH$_2$)$_3$PPh$_2$)] (OAc)$_2$ (Ph=phenyl, Ac=acetyl), is used. The carbon monoxide copolymerization can be carried out in suspension, as described in EP-A 0 305 011, or in the gas phase, for example according to EP-A 0 702 045. Frequently used suspension media are on the one hand low molecular weight alcohols, in particular methanol (cf. also EP-A 0 428 228), and on the other hand nonpolar or polar aprotic liquids such as dichloromethane, toluene or tetrahydrofuran (cf. EP-A 0 460 743 and EP-A 0 590 942). Complex compounds having bisphosphine chelate ligands whose radicals on the phosphorus atom are aryl or substituted aryl groups have proven particularly suitable for said polymerization process. Accordingly, 1,3-bis(diphenylphosphino)propane or 1,3-bis[di-(o-methoxyphenyl)phosphino]propane is particularly frequently used as a chelate ligand (cf. also Drent et al., Chem. Rev. 96 (1996), 663–681). Usually, the carbon monoxide copolymerization is carried out in the presence of acids.

The carbon monoxide copolymerization in low molecular weight alcohols, such as methanol, has the disadvantage that the resulting carbon monoxide copolymer absorbs up to 80% by volume of, for example, methanol. Accordingly, a large amount of energy is required to dry the resulting carbon monoxide copolymer and to isolate it in pure form. Another disadvantage is that, even after an intensive drying process, residual amounts of alcohol still remain in the carbon monoxide copolymer. Molding materials prepared in this manner are thus from the outset unsuitable for use as packaging materials for food. EP-A 0 485 035 proposes the use of additions of water in amounts of from 2.5 to 15% by weight to the alcoholic suspending medium in order to eliminate the residual amounts of low molecular alcohol in the carbon monoxide copolymer. However, this procedure, too, does not lead to methanol-free copolymers. On the other hand, the use of halogenated hydrocarbons or aromatics, such as dichloromethane or chlorobenzene or toluene, gives rise to problems particularly in disposal.

To overcome the disadvantages associated with said suspending media, Jiang and Sen, Macromolecules 27 (1994), 7215–7216, describe the preparation of linear, alternating carbon monoxide copolymers in aqueous systems using a catalyst system consisting of [Pd(CH$_3$CN)$_4$] (BF$_4$)$_2$ and 1,3-bis[di(3-sulfophenyl)phosphino]propane as water-soluble chelate ligands. However, the catalyst activity achieved is very low and therefore unsuitable for a large-scale industrial preparation.

Compared with Jiang and Sen, Verspui et al., Chem. Commun. (1998), 401–402, achieve an increase in the catalyst activity in the copolymerization of carbon monoxide and ethene by using said chelate ligands in substantially purer form as a result of an improved synthesis method (cf. also Hermann et al., Angew. Chem. Int. Ed. Engl. 34 (1995) 811 et seq.). Furthermore, the presence of a Brönsted acid is required in order to obtain catalyst activities improved in comparison with Jiang and Sen. Although it is actually possible to prepare the chelate ligand 1,3-bis[di(3-sulfophenyl)phosphino]propane in purer form with the aid of an improved synthesis method, this does not provide a route to suitable chelate ligands having other substitution patterns. Thus, the water-soluble transition metal complexes described are limited exclusively to sulfonated aromatic substituents on phosphorus. Preparation of these chelate ligands furthermore requires the handling of very aggressive substances, such as boric acid, concentrated sulfuric acid and oleum. Owing to the given structure, an extension to other systems is in principle not possible.

It is therefore desirable, for the copolymerization of carbon monoxide and α-olefinically unsaturated compounds in aqueous systems, to be able to rely on metal complexes which should from the outset permit a large number of different substituents on chelate ligands and at the same time enable constantly good reproducibility in combination with high efficiency.

It is an object of the present invention to provide water-soluble transition metal complexes which are suitable as the active component of a catalyst system for the preparation of linear, alternating carbon monoxide copolymers in aqueous media.

We have found that this object is achieved by the water-soluble transition metal complexes defined at the outset. We have also found a process for the preparation of these transition metal complexes and their use for the preparation of linear, alternating carbon monoxide copolymers.

We have furthermore found water-soluble chelate ligands, a process for the preparation of these chelate ligands and their use for the preparation of water-soluble transition metal complexes.

Preferred novel water-soluble transition metal complexes are based on compounds of the formula (Ia)

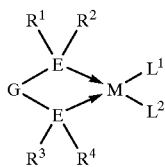
(Ia)

where

G is —(CR$^b_2$)$_r$— or —(CR$^b_2$)—N(R$^5$)—(CR$^b_2$)—, where R$^b$ is hydrogen, C$_1$- to C$_{10}$-alkyl or C$_6$- to C$_{10}$-aryl, r is 1, 2, 3 or 4, R$^5$ is hydrogen, C$_1$- to C$_{10}$-alkyl, C$_3$- to C$_{10}$-cycloalkyl, C$_6$- to C$_{15}$-aryl or C$_1$- to C$_{10}$-alkyl, C$_3$- to C$_{10}$-cycloalkyl or C$_6$- to C$_5$-aryl, which is substituted by functional groups based on elements of groups IVA, VA, VIA and VIIA of the Periodic Table of Elements, m is palladium or nickel, E$^1$ and E$^2$ are each phosphorus, R$^1$ to R$^4$ are linear, branched or carbocycle-containing C$_2$- to C$_{28}$-alkyl units or C$_3$- to C$_{14}$-cycloalkyl units which have at least one terminal or internal hydroxyl, amino acid, carboxyl, phosphoric acid, ammonium or sulfonic acid group, or alkylaryl where the alkyl moiety is of 1 to 20 carbon atoms and the aryl moiety is of 6 to 15 carbon atoms, the alkyl or aryl moiety being substituted by at least one hydroxyl, carboxyl, amino acid, phosphoric acid, ammonium or sulfonic acid group, L$^1$ and L$^2$ are each acetate, trifluoroacetate, tosylate or halide, and p, m, n are each 0.

In principle, bidentate chelate ligands of the formula (R$^1$)(R$^2$) E$^1$—G—E$^2$ (R$^3$) (R$^4$) (III), in which the substituents and indices have the abovementioned meanings, are suitable as a component of the transition metal complex (I).

The bridging structural unit G in the novel metal complexes (I) or the chelate ligand (III) consists in general of monoatomic or polyatomic linking segments. A bridging structural unit is understood in principle as meaning a group which links the elements E$^1$ and E$^2$ to one another. Such structural units include, for example, substituted or unsubstituted alkylene chains or those alkylene chains in which an alkylene unit is replaced by a silylene group, amino, phosphino or an ether oxygen.

The preferred monoatomically bridged structural units are those having a bridging atom from group IVA of the Periodic Table of Elements, such as —C(R$^b$)$_2$— or —Si(R$^a$)$_2$—, where R$^a$, independently of one another, are in particular each linear or branched C$_1$- to C$_{10}$-alkyl, for example methyl, ethyl, i-propyl or t-butyl, C$_3$- to C$_6$-cycloalkyl, such as cyclopropyl or cyclohexyl, C$_6$ to C$_{10}$-aryl, such as phenyl or naphthyl, C$_6$- to C$_{10}$-aryl substituted by functional groups based on nonmetallic elements of groups IVA, VA, VIA or VIIA of the Periodic Table, for example tolyl, (trifluoromethyl)phenyl, dimethylaminophenyl, p-methoxyphenyl or partially halogenated or perhalogenated phenyl, aralkyl where the alkyl moiety is of 1 to 6 carbon atoms and the aryl moiety is of 6 to 10 carbon atoms, for example benzyl, and R$^b$ are in particular each hydrogen and may furthermore have the meanings stated above for R$^a$. R$^a$ is in particular methyl and R$^b$ is in particular hydrogen.

Among the polyatomically bridged systems, the diatomically, triatomically and tetraatomically bridged structural units are noteworthy, the triatomically bridged systems generally being preferably used.

Suitable triatomically bridged structural units are based in general on a chain of carbon atoms, for example propylene (—CH$_2$CH$_2$CH$_2$—), or on a bridge unit having a heteroatom from group IVA, VA or VIA of the Periodic Table of Elements, such as silicon, nitrogen, phosphorus or oxygen, in the chain skeleton.

The bridge carbon atoms may be substituted in general by C$_1$- to C$_6$-alkyl, such as methyl, ethyl or t-butyl, by C$_6$- to C$_{10}$-aryl such as phenyl or by functional groups based on elements of groups IVA, VA, VIA or VIIA of the Periodic Table of Elements, for example triorganosilyl, dialkylamino, alkoxy, hydroxyl or halogen. Suitable substituted propylene bridges are, for example, those having a methyl, phenyl, hydroxyl, trifluoromethyl, co-hydroxyalkyl or methoxy group in the 2 position.

Among the polyatomically bridged structural units having a heteroatom in the chain skeleton, advantageously used compounds are those in which Z is nitrogen or phosphorus, in particular nitrogen (cf. also formula (I)). R$^5$ on Z may be in particular hydrogen, linear or branched C$_1$- to C$_{28}$-alkyl, such as methyl, ethyl, isopropyl, tert-butyl, n-hexyl or n-dodecyl, C$_3$- to C$_{14}$-cycloalkyl, in particular C$_3$- to C$_8$-cycloalkyl, such as cyclopropyl or cyclohexyl, C$_6$- to C$_{15}$-aryl, in particular C$_6$- to C$_{10}$-aryl, for example phenyl, or alkylaryl where the alkyl radical is of 1 to 20 carbon atoms and the aryl radical is of 6 to 10 carbon atoms, for example benzyl.

Said alkyl and aryl radicals include both unsubstituted and substituted compounds. The substituted compounds may be, for example, functional groups based on elements of groups IVA, VA, VIA or VITA of the Periodic Table of Elements. Inter alia, triorganosilyl groups, such as trimethylsilyl or tert-butyldiphenylsilyl, the carboxyl group or carboxylic acid derivatives, such as esters or amides, primary, secondary or tertiary amino, such as dimethylamino or methylphenylamino, the nitro and the hydroxyl group and furthermore alkoxy, methoxy or ethoxy, the sulfonate group and halogen, such as fluorine, chlorine or bromine, are suitable. For the purposes of the present invention aryl includes substituted and unsubstituted hetaryl, for example pyridyl or pyrrolyl. Alkyl radicals $R^5$ also include long-chain alkylene having 12 to 22 carbon atoms in the chain, which may have polar protic or ionic functional groups, such as the sulfo, carboxyl, hydroxyl, amino acid or ammonium group, for example in a terminal position.

Preferred radicals $R^5$ include those compounds which constitute an electron-attracting substituent. Suitable electron-attracting substituents are, for example, alkyl groups having one or more electron-attracting radicals, such as fluorine, chlorine, nitrile or nitro α or β to Z. Aryl groups having said electron-attracting radicals and, as radicals bonded directly to Z, also the nitrile, sulfonate and nitro group are furthermore suitable. Examples of suitable electron-attracting alkyl radicals are trifluoromethyl, trichloroethyl, difluoromethyl, 2,2,2-trifluoroethyl, nitromethyl and cyanomethyl. Examples of suitable electron-attracting aryl radicals are m-, p- and o-fluoro- and chlorophenyl, 2,4-difluorophenyl, 2,4-dichlorophenyl, 2,4,6-trifluorophenyl, 3,5-bis(trifluoromethyl)phenyl, nitrophenyl, 2-chloro-5-nitrophenyl and 2-bromo-5-nitrophenyl. In this context, carbonyl units are also suitable radicals $R^5$, so that, if Z is nitrogen, Z and $R^5$ form a carboxamide functional group. A suitable radical of this type is acetyl or trifluoroacetyl.

$R^5$ is particularly preferably tert-butyl, phenyl, p-trifluorophenyl, trifluoromethyl, 2,2,2-trifluoroethyl, pentafluorophenyl, 3,5-bis(trifluoromethyl)phenyl or ortho-difluorophenyl, e.g. 3,4-difluorophenyl, meta-difluorophenyl, e.g. 2,4-difluorophenyl, or para-difluorophenyl, e.g. 2,5-difluorophenyl.

Suitable units A' and B' according to the formulae (I) to (III) are $C_1$- to $C_4$-alkylene units in substituted or unsubstituted form, for example methylene, ethylene, propylene or ethylidene, propylidene and benzylidene. Methylene, ethylene, ethylidene and benzylidene are preferred, methylene being particularly preferably used.

A' and B' may also be a monoatomic, diatomic or triatomic or tetraatomic component of an aliphatic or aromatic ring system. For example, A' and B' may be a methylene or ethylene unit of a cyclopropyl, cyclopentyl or cyclohexyl ring. Aliphatic and aromatic heterocyclic structures are also suitable ring systems.

A' and B' may furthermore be part of a heterocyclic structure which is formed from the components A'—Z—$R^5$ and B'—Z—$R^5$, i.e. A'—Z—$R^5$ and B'—Z—$R^5$ may form, for example, a substituted or unsubstituted pyrrolidine or piperidine ring.

Suitable chelating atoms $E^1$ and $E^2$ are, independently of one another, the nonmetallic elements of group VA of the Periodic Table of Elements, nitrogen and phosphorus being preferably used, in particular phosphorus. In a preferred embodiment, $E^1$ and $E^2$ in the compounds (I) and (III) are each phosphorus.

In the novel transition metal complexes, $R^1$ to $R^4$ are each $C_2$- to $C_{20}$-alkyl, $C_3$- to $C_{14}$-cycloalkyl, preferably $C_3$- to $C_8$-cycloalkyl, or alkylaryl where the alkyl moiety is of 1 to 28 carbon atoms and the aryl moiety is of 6 to 15 carbon atoms, each of which is substituted by at least one polar protic or ionic functional group based on elements of groups IVA to VIA of the Periodic Table of Elements. $R^1$ to $R^4$ are preferably linear, branched or carbocycle-containing $C_2$- to $C_{28}$-alkyl or $C_3$- to $C_{14}$-cycloalkyl units which have at least one terminal or internal hydroxyl, carboxyl, phosphoric acid, ammonium, amino acid or sulfonic acid group, or are alkylaryl where the alkyl moiety is of 1 to 28 carbon atoms and the aryl moiety is of 6 to 15 carbon atoms, the alkyl or aryl moiety is substituted by at least one hydroxyl, carboxyl, phosphoric acid, ammonium, amino acid or sulfonic acid group.

The salts of the carboxylic acids, phosphoric acids, amino acids or sulfonic acids may also be used. Suitable salts are, for example, alkali metal or alkaline earth metal salts, such as sodium, potassium or magnesium carboxylates or sulfonates. Suitable alkyl radicals $R^1$ to $R^4$ are, for example, alkylene units having one or two terminal hydroxyl, carboxyl, sulfo or ammonium groups. $R^1$ to $R^4$ may also have more than two polar groups, for example four or six hydroxyl, ammonium or carboxyl groups. Accordingly, $R^1$ to $R^4$ in a chelate compound (III) may each also have different functional groups. Furthermore, $R^1$ to $R^4$ may have functional groups in numbers differing from one another. Suitable radicals $R^1$ to $R^4$ are accordingly compounds of the formula (IV)

$$—(CR^d{}_2)_k—(T)_l—(CR^d{}_2)_{k'}—Y \qquad (IV),$$

where $R^d$ is the same as $R^b$, or Y,

T is $C_3$- to $C_{10}$-cycloalkylene, in particular $C_3$- to $C_6$-cycloalkylene, or $C_6$- to $C_{15}$-arylene, in particular $C_6$- to $C_{10}$-arylene, unsubstituted or substituted by $R^d$ or Y, k is from 0 to 20 if 1 is 0 or 1 is 1 and T is cycloalkyl and is from 1 to 20 if 1 is 1 and T is aryl, k' is from 0 to 20, l is 0 or 1 and Y is a polar protic or ionic functional group based on elements of groups IVA to VIA of the Periodic Table of Elements.

Suitable radicals Y are the hydroxyl, amino acid, carboxyl, phosphoric acid, ammonium and sulfonic acid group. Preferred cycloaliphatic radicals T are cyclopropyl and cyclohexyl and a preferred aryl or arylene unit T is phenyl(ene). k is preferably from 2 to 20, especially from 3 to 18, and k' is preferably from 0 to 10, in particular from 1 to 8.

The novel water-soluble chelate ligands of the formula (III) $(R^1)$ $(R^2)E^1$—G—$E^2(R^3)$ $(R^4)$ are obtained, for example, a) by converting a compound of the formula (IIIa)

$$L—(CR^b{}_2)_r—L \text{ or } L—(CR^b{}_2)—N(R^5)—(CR^b{}_2)—L \qquad (IIIa),$$

where $R^b$ is hydrogen, $C_1$- to $C_{10}$-alkyl or $C_6$- to $C_{10}$-aryl, r is 1, 2, 3 or 4, $R^5$ is hydrogen, $C_1$- to $C_{10}$-alkyl, $C_3$- to $C_{10}$-cycloalkyl, $C_6$- to $C_{15}$-aryl or $C_1$- to $C_{10}$-alkyl, $C_3$- to $C_{10}$- cycloalkyl or $C_6$- to $C_{15}$-aryl substituted by functional groups based on the elements of groups IVA, VA, VIA and VIIA of the Periodic Table of Elements and L, independently of one another, are each chloride, bromide or iodide, by means of an Arbuzov reaction with a trialkoxyphosphine into a compound of the formula (IIIb) where L is $P(L')_3$ and L' is $O-C_1$- to $O-C_6$-alkyl, $O-C_6$- to $O-C_{10}$-aryl or $O$—alkylaryl where the alkyl moiety is of 1 to 6 carbon atoms and the aryl moiety is of 6 to 20 carbon atoms, b) reducing the compound (IIIb) to the compound of the formula (IIIc), where L' is hydrogen, and c) subjecting the compound of the formula (IIIc) to free radical polymerization in the presence of at least four equivalents of an olefinically unsaturated compound which has at least one polar protic or ionic functional group based on nonmetallic elements of groups IVA to VIA of the Periodic Table of Elements.

It is preferable to use an olefinically unsaturated compound of the formula (IVa)

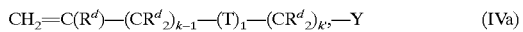
$$CH_2=C(R^d)-(CR^d_2)_{k-1}-(T)_l-(CR^d_2)_{k'}-Y \qquad (IVa)$$

where $R^d$, independently of one another, are each hydrogen, $C_1$- to $C_{20}$-alkyl, $C_3$- to $C_{10}$-cycloalkyl, $C_6$- to $C_{15}$-aryl or alkylaryl where the alkyl moiety is of 1 to 10 carbon atoms and the aryl moiety is of 6 to 15 carbon atoms, and may additionally be Y, T is $C_3$- to $C_{10}$-cycloalkylene, in particular $C_3$- to $C_6$-cycloalkylene, or $C_6$- to $C_{15}$-arylene, in particular $C_6$- to $C_{10}$-arylene, unsubstituted or substituted by $R^d$ or Y, k is from 1 to 20 if l is 0 or l is 1 and T is cycloalkyl and is from 2 to 20 if l is 1 and T is aryl, k' is from 0 to 20, l is 0 or 1 and Y is a polar protic or ionic functional group based on elements of groups IVA to VIA of the Periodic Table of Elements.

For the preparation of, for example, propylene-bridged (G=—($CH_2)_3$—) chelate ligand compounds (III), it is usual to start from commercially available 1,3-dibromopropane. A double Arbuzov reaction, for example with trimethoxy- or triethoxyphosphine, gives 1,3-bisphosphonic acid derivatives, which can be reduced, as described in Methoden der organischen Chemie (Houben-Weyl), 4th edition, Volume XII/1, part 1, Georg Thieme Verlag, 1963, page 62, to 1,3-diphosphinopropane. A suitable reducing agent is, for example, lithium aluminum hydride or diisobutylaluminum hydride. Via a hydrophosphination reaction with said functional olefins, 1,3-diphosphinopropane provides a flexible route to substituted bisphosphine chelate ligands. The hydrophosphination takes place in general via a free radical mechanism and can be initiated thermally or photochemically or with the aid of a free radical initiator. In general, temperatures of from 20 to 100° C. and pressures of from 0.1 to 5 bar are required for thermal initiation. A suitable free radical initiator is, for example, di-tert-butyl peroxide or azobisisobutyronitrile. For the photochemical initiation, as a rule UV radiation from a high-pressure mercury lamp over a period of from 2 to 48 hours is sufficient for a quantitative hydrophosphination. The last-mentioned process is as a rule preferred. Processes involving free radical initiation generally give anti-Markovnikov products in the hydrophosphination.

Suitable chelate ligand compounds can also be prepared under conditions of acidic catalysis. Owing to the isomerization of the olefin double bond under the acidic reaction conditions, the products obtained by this process frequently occur as a mixture. The hydrophosphination step in the process is described, for example, in Methoden der organischen Chemie (Houben-Weyl), 4th edition, Volume XII/1, part 1, Georg Thieme Verlag, 1963, pages 25 to 28.

For the preparation of chelate ligands having the radicals $R^1$ to $R^4$ which carry carboxyl groups, it has proven advantageous to start from olefinically unsaturated compounds which have been derivatized with corresponding carboxylic ester groups and subsequently to use these in the hydrophosphination reaction. The free carboxylic acids can be obtained by hydrolysis by known methods.

According to the invention, all olefins which are covered by this class of compounds are suitable for said hydrophosphination reaction, provided that they have a polar protic or ionic functional group. For example, $C_3$- to $C_{28}$-alkenes having at least one internal or terminal double bond and at least one hydroxyl, amino acid, carboxyl, phosphoric acid, ammonium or sulfonic acid group are suitable. Olefinic compounds having aromatic radicals are also suitable, it being possible for the functional group to be both on the aliphatic and on the aromatic radical, for example 4-(1-pentenyl)benzoic acid or 3-phenyl-pent-5-enecarboxylic acid. Olefinic compounds having aliphatic carbocycles in the alkylene chain or as substituent are furthermore suitable. Moreover, cyclic olefins, such as cyclohexen-3-ol or cycloocten-4-ol, may also be used. It is of course also possible to use olefins having a plurality of polar protic or ionic functional groups. Suitable α-olefinic compounds are preferably used in the hydrophosphination reaction of the α,ω-bisphosphines. Suitable compounds of this type are, for example, also heteroatom-containing α-olefins, such as (meth)acrylates or (meth)acrylamides and homoallyl- or allyl alcohols.

Radicals $R^1$ to $R^4$ in which the hydrophilic character induced by the polar protic or ionic functional groups is sufficient to render the metal complex (I) completely water-soluble are particularly preferably used. The larger the number of functional groups on the radicals $R^1$ to $R^4$, the greater may also be the lipophilic aliphatic or aliphatic-aromatic fraction. For example, preferred radicals $R^1$ to $R^4$ each having a hydroxyl group are those having 2 to 15 carbon atoms in the alkyl unit.

In a particularly preferred embodiment of the chelate ligands (III), $R^1$ to $R^4$ as alkyl substituents with a hydroxyl group have 4 to 12, in particular 4 to 7, carbon atoms, $R^1$ to $R^4$ as alkyl substituents with a carboxyl group have 4 to 15, in particular 5 to 12, carbon atoms, $R^1$ to $R^4$ as alkyl substituents with a sulfonic acid group have 4 to 18, in particular 5 to 15, carbon atoms and $R^1$ to $R^4$ as alkyl substituents with an ammonium group have 4 to 22, in particular 5 to 20, carbon atoms.

Examples of suitable chelate ligands (III) are 1,3-bis(di-5-hydroxypentyl)phosphinopropane, 1,3-bis(di-6-hydroxyhexyl)phosphinopropane, 1,3-bis(di-7-hydroxyheptyl)phosphinopropane, 1,3-bis(di-8-hydroxyoctyl)phosphinopropane, 1,3-bis(di(3-hydroxycyclopentyl)propyl) phosphinopropane, 1,3-bis[di-5-sulfopentyl]phospinopropane, 1,3-bis[di-6-sulfohexyl]phosphinopropane, 1,3-bis[di-7-sulfoheptyl]phosphinopropane, 1,3-bis[di-8-sulfooctyl]phosphinopropane, 1,3-bis[di(3-sulfocyclopentyl)propyl]phosphinopropane,
1,3-bis(di-5-pentanoyl)phosphinopropane,
1,3-bis(di-6-hexanoyl)phosphinopropane,
1,3-bis(di-7-heptanoyl)phosphinopropane,
1,3-bis(di-8-octanoyl)phosphinopropane,
bis[(di-5-hydroxypentyl)phospinomethyl]phenylamine,
bis[(di-6-hydroxyhexyl)phosphinomethyl]phenylamine,
bis[(di-7-hydroxyheptyl)phosphinomethyl]phenylamine,
bis[(di-8-hydroxyoctyl)phosphinomethyl]phenylamine,
bis[(di(3-hydroxycyclopentyl)propyl]phenylamine,
bis[(di-5-sulfopentyl)phosphinomethyl]phenylamine,
bis[(di-6-sulfohexyl)phospinomethyl]phenylamine,
bis[(di-7-sulfoheptyl)phosphinomethyl]phenylamine,
bis[(di-8-sulfooctyl)phosphinomethyl]phenylamine,
bis[(di-3-sulfocyclopentyl) propyl]phospinomethyl] phenylamine,
bis[(di-5-pentanoylphospinomethyl]phenylamine,
bis[(di-6-hexanoyl)phospinomethyl]phenylamine,
bis[(di-7-heptanoyl)phosphinomethyl]phenylamine and
bis[(di-8-octanoyl)phosphinomethyl]phenylamine.

Particularly preferred among said chelate ligand compounds are those in which $R^1$ to $R^4$ are a hexyl, octyl, cyclopentyl or cyclohexyl radical substituted by a hydroxyl or carboxyl group.

Suitable metals M of the novel transition metal complexes are the metals of groups VIIIB, IB and IIB of the Periodic Table of Elements, i.e. chiefly the platinum metals, such as ruthenium, rhodium, osmium, iridium and platinum and very particularly preferably palladium, in addition to iron, cobalt and nickel. In the complexes (I), the metals may be formally uncharged, formally bearing a single positive charge or preferably formally bearing a double positive charge.

Suitable formally charged inorganic ligands $L^1$ and $L^2$ are hydride, halides, sulfates, phosphates or nitrates. Carboxylates or salts of organic sulfonic acids, such as methylsulfonate, trifluoromethylsulfonate or p-toluenesulfonate, are also suitable. Among the salts of organic sulfonic acids, p-toluenesulfonate is preferred. Preferred formally charged ligands $L^1$ and $L^2$ are carboxylates, preferably $C_1$- to $C_{20}$-carboxylates, in particular $C_1$- to $C_7$-carboxylates, e.g. acetate, trifluoroacetate, propionate, oxalate, citrate or benzoate. Acetate is particularly preferred.

Other suitable formally charged organic ligands $L^1$ and $L^2$ are aliphatic $C_1$ to $C_{20}$ radicals, cycloaliphatic $C_3$ to $C_{30}$ radicals, $C_7$- to $C_{20}$-aralkyl radicals having $C_6$- to $C_{14}$-aryl radicals and $C_1$- to $C_6$-alkyl radicals and aromatic $C_6$- to $C_{20}$ radicals, for example, methyl, ethyl, propyl, isopropyl, tert-butyl, n-pentyl, i-pentyl, cyclohexyl, benzyl, phenyl, and aliphatically or aromatically substitued phenyl radicals.

Suitable formally uncharged ligands $L^1$ and $L^2$ are in general Lewis bases, i.e. compounds having at least one free electron pair. Lewis bases whose free electron pair or free electron pairs is or are present on a nitrogen or oxygen atom are particularly suitable, for example nitriles, R-CN, ketones, ethers, alcohols or water. $C_1$- to $C_{10}$-nitriles, such as acetonitrile, propionitrile or benzonitrile, or $C_2$- to $C_{10}$-ketones, such as acetone or acetylacetone, or $C_2$- to $C_{10}$-ethers, such as dimethyl ether, diethyl ether or tetrahydrofuran, are preferably used. In particular, acetonitrile or tetrahydrofuran is used.

In principle, the ligands $L^1$ and $L^2$ may be present in any desired ligand combination, i.e. the metal complex (I) may, for example, contain a nitrate or an acetate radical, a p-toluenesulfonate and an acetate radical or a nitrate ligand or a formally charged organic ligand, such as tert-butyl. $L^1$ and $L^2$ are preferably present as identical ligands in the metal complexes.

Depending on the formal charge of the complex fragment containing the metal M, the metal complexes contain anions X. If the M-containing complex fragment is formally uncharged, however, the novel complex (I) contains no anion X. Advantageously used anions X are those which have very little nucleophilic character, i.e. very little tendency to form a chemical bond with the central metal M.

Suitable anions X are, for example, perchlorate, sulfate, phosphate, nitrate and carboxylates, for example acetate, trifluoroacetate, trichloroacetate, propionate, oxalate, citrate and benzoate, and conjugated anions of organosulfonic acids, for example methylsulfonate, trifluoromethylsulfonate and para-toluenesulfonate, and furthermore tetrafluoroborate, tetraphenylborate, tetrakis (pentafluorophenyl)borate, tetrakis[bis(3,5-trifluoromethyl) phenyl]borate, hexafluorophosphate, hexafluoroarsenate or hexafluoroantimonate. Perchlorate, trifluoroacetate, sulfonates, such as methylsulfonate, trifluoromethylsulfonate, p-toluenesulfonate, tetrakis[bis(3,5-trifluoromethyl)phenyl]borate, tetrafluoroborate or hexafluorophosphate are preferably used, in particular trifluoromethylsulfonate, trifluoroacetate, perchlorate or p-toluenesulfonate.

For example, suitable defined transition metal complexes are:

[1,3-bis(di-5-hydroxypentyl)phospinopropane]palladium (II) acetate,

[1,3-bis(di-6-hydroxyhexyl)phosphinopropane]palladium (II) acetate,

[1,3-bis(di(3-hydroxycyclopentyl)propyl) phosphinopropane]palladium(II) acetate,

[1,3-bis(di-8-hydroxyoctyl)phospinopropane]palladium (II) acetate and

[1,3-bis(di(3-hydroxycyclohexyl)propyl) phospinopropane]palladium (II) acetate.

The transition metal complexes described are soluble in water, at least in small amounts. As a rule, these metal complexes are readily to very readily soluble in water.

Defined transition metal complexes (I) can be prepared by the following processes.

The preparation is carried out for the neutral chelate complexes (p=0) by exchanging weakly coordinating ligands for example 1,5-cyclooctadiene, benzonitrile or tetramethylethylenediamine, which are bonded to the corresponding transition metal compounds, for example transition metal halides, transition metal (alkyl)(halides) or transition metal-diorganyls, for the novel chelate ligands of the formula (III) having the meanings described above.

The reaction is carried out in general in a polar solvent, for example acetonitrile, acetone, ethanol, diethyl ether, dichloromethane or tetrahydrofuran, or mixtures thereof at from −78 to +60° C.

Furthermore, neutral metal complexes (I) in which $L^1$ and $L^2$ are carboxylate, e.g. acetate, can be prepared by reacting transition metal salts, for example Pd(OAc)$_2$, with the chelate ligands (III) described in acetonitrile, acetone, ethanol, diethyl ether, dichloromethane, tetrahydrofuran or water at room temperature. Solvent mixtures may also be used.

Another suitable method of synthesis is the reaction of the chelate complexes of the formula (I) with organometallic compounds of groups IA, IIA, IVA and IIB, for example $C_1$- to $C_6$-alkyls of the metals lithium, aluminum, magnesium, tin or zinc, formally charged inorganic ligands $L^1$ and $L^2$ as defined above being exchanged for formally charged aliphatic, cycloaliphatic or aromatic ligands $L^1$ and $L^2$ as likewise defined above. The reaction is carried out in general in a solvent, for example diethyl ether or tetrahydrofuran, at from −78 to 65° C.

Monocationic complexes of the formula (I) (p=1) can be obtained, for example, by reacting (chelate ligand)metal (acetate)(organo) or (chelate ligand)metal(halo)(organo) complexes with stoichiometric amounts of a metal salt M'X. The reactions are carried out in general in coordinating solvents, for example acetonitrile, benzonitrile or tetrahydrofuran, at from −78 to 65° C.

It is advantageous if the metal salts M'X fulfil the following criteria. The metal M' should preferably form sparingly soluble metal chlorides, for example silver chloride. The salt anion should preferably be a nonnucleophilic anion X as defined above.

Suitable salts for the formation of the cationic complexes are silver tetrafluoroborate, silver hexafluorophosphate, silver trifluoromethanesulfonate, silver perchlorate, silver paratoluenesulfonate, silver trifluoroacetate and silver trichloroacetate.

The dicationic complexes (p=2) are prepared similarly to the monocationic complexes except that, instead of the (chelate ligand)metal(acetate)(organo) or the (chelate ligand)metal(halo)(organo) complexes, the (chelate ligand) metal (diacetate) or (chelate ligand)metal(dihalo) complexes are now used as the intermediates.

Another suitable process for the preparation of the dicationic complexes (I) is the reaction of $[Q_4M]X_2$ with the chelate ligands of the formula (III) which are defined at the outset. Here, Q are identical or different weak ligands, for example acetonitrile, benzonitrile or 1,5-cyclooctadiene, and M and X have the meanings defined above.

A preferred process for the preparation of the metal complexes of the formula (I) is the reaction of the dihalometal precursor complexes with silver salts containing non-coordinating anions.

The novel water-soluble transition metal complexes can be used as an essential component of a catalyst system for the copolymerization of carbon monoxide and α-olefinically unsaturated compounds in particular in aqueous media. As a further constituent of the catalyst system, a Lewis or protic acid can be used as an activator component.

The novel water-soluble transition metal complexes have a constantly high average catalyst activity even after a reaction time of several hours.

The Examples which follow illustrate the invention.

EXAMPLES

I) Preparation of the Chelate Ligand Compounds
General Procedure
  i) Preparation of Propane-1,3-bis(diethylphosphonite)
  Triethyl phosphite (696 ml) was added to 1,3-dibromopropane (102.5 ml) and slow heating to 140° C. was carried out. The resulting bromoethane was removed by distillation. After the release of bromoethane had declined, the reaction temperature was increased to 155° C. and the reaction was maintained at this temperature for 24 hours. Further triethyl phosphite (696 ml) was added dropwise and the reaction was stopped after 24 hours by separating off excess triethyl phosphite by distillation. Monosubstituted product was removed by distillation at 150° C. under greatly reduced pressure. The remaining distillation residue comprised propane-1,3-bis(diethylphosphonite). Yield: 86%.

ii) Preparation of 1,3-Diphosphinopropane
  A solution of propane-1,3-bis(diethylphosphonite) (103.3 g) in absolute diethyl ether (100 ml) was slowly added at 0° C. to a suspension of $LiAlH_4$ (25 g) in diethyl ether (200 ml). After the end of the addition, the reaction temperature was brought to room temperature and the reaction mixture was stirred for 16 hours at this temperature. To hydrolyze excess $LiAlH_4$, degassed 6 molar hydrochloric acid saturated with argon was added slowly. The organic phase separated off was dried over sodium sulfate. The aqueous phase was mixed thoroughly with diethyl ether and, after phase separation, the diethyl ether phase was dried over sodium sulfate and combined with the abovementioned organic phase. 1,3-Diphosphinopropane was obtained by distillation at 140° C. under atmospheric pressure. Yield: 61%.

iii) Preparation of Water-soluble Chelate Ligand Compounds
  Bis(di-7-hydroxyheptyl)phosphinopropane, 1,3-diphosphinopropane (1.08 g) and 6-hepten-1-ol (44 mmol) which was repeatedly degassed and saturated with argon were exposed in suspended quartz tube for 24 hours to UV light from a high-pressure mercury lamp. In the case of higher olefins, the reaction vessel was additionally heated in order to reduce the viscosity of the reaction mixture. The desired chelate ligand compound was obtained virtually quantitatively by separating off the excess olefin component by distillation.

Bis(di-5-hydroxypentyl)-, bis(di-6-hydroxyhexyl)-, bis(di-8-hydroxyoctyl)- and bis(di(3-hydroxycyclopentyl) propyl)phosphinopropane were obtained similarly to the abovementioned method.

The starting compounds 1-pentenol, 1-hexenol and 3-hydroxy-3-cyclopentylpropene were obtained as follows:
    4-Penten-1-ol was prepared by means of $LiAlH_4$ reduction of 4-pentenoic acid, commercially available from Aldrich. 6-Heptenoic acid and 7-octenoic acid were converted into 6-hepten-1-ol and 7-octen-1-ol, respectively, by a similar method.
  5-Hexen-1-ol was obtained from Fluka and was used without further purification. 3-Hydroxy-3-cyclopentylpropene was prepared from allylmagnesium chloride and cyclopentane via a Grignard reaction.

II) Preparation of Defined Transition Metal Complexes
  i) Preparation of
  [1, 3-bis (di-5-hydroxypentyl)phosphinopropane] palladium(II) acetate
  0.9 g of 1,3-bis (di-5-hydroxypentyl)phophinopropane was dissolved in 10 ml of repeatedly degassed ethanol saturated with argon and was slowly added dropwise to a solution of palladium(II) acetate (0.44 g in 15 ml of degassed acetonitrile saturated with argon). To complete the reaction, stirring was carried out at room temperature for a further 20 minutes. The solvent mixture was removed under reduced pressure and the defined Pd complex was isolated as a brown-yellow, highly viscous oil.
  ii) Preparation of
  [1,3-bis (di-6-hydroxyhexyl)phosphinopropane] palladium(II) acetate
  The reaction was carried out similarly to II) I). The chelate ligand used was 1,3-bis (di-6-hydroxyhexyl) phosphinopropane.
  iii) Preparation of
  [1,3-bis (di(3-hydroxycyclopentyl)propyl) phosphinopropane]palladium(II) acetate
  A mixture of
  1,3-bis (di(3-hydroxycyclopentyl)propyl) phosphinopropane in 20 ml of dichloromethane was added dropwise at room temperature to a solution of 0.25 g of palladium(II) acetate in 20 ml of acetonitrile. After stirring at room temperature for 16 hours, the solvent mixture was removed under reduced pressure. The desired Pd complex was isolated as a red solid.

Comparative experiments submitted for International Application WO 00/01708:

The chelate ligand dppp-SO$_3$Na (=C$_3$H$_6$-1,3-[P(C$_6$H$_4$-m-SO$_3$Na)$_2$]$_2$) was synthesized by a method due to Verspui et al., Chem. Commun., 1998, 401 to 402.

The defined catalyst complex [Pd(dppp-SO$_3$Na) (acetate)$_2$] was obtained by method II) i) of WO 00/01756 (also see page 20, line 41 to page 21, line 8) via the reaction of equimolar amounts of Pd(acetate)$_2$ and dppp-SO$_3$Na.

Copolymerization of Carbon Monoxide and Ethene

Distilled water (100 ml), the desired amount of [1,3-bis-(di-6-hydroxyhexyl)phosphinopropane]palladium(II) acetate and p-toluenesulfonic acid (five times molar amount, based on the amount of catalyst used) were introduced into a 300 ml autoclave. The reaction vessel was first evacuated and flooded with nitrogen. The nitrogen atmosphere was displaced by a carbon monoxide/ethene mixture (1:1) and the polymerization was carried out at the desired pressure and the desired temperature over a preselected period at a stirring speed of 300 rpm. The reaction conditions were kept constant during the polymerization. The reaction was stopped by cooling and letting down the reaction vessel. The copolymer separated off by filtration was washed with methanol (500 ml) and acetone (200 ml) and dried at 80° C. over a period of 5 hours under high vacuum.

Data on the copolymerization parameters and results are shown in Table 1 below:

| Comparative Experiment | Amount of catalyst [mmol] | Duration [h] | Pressure [bar] | Temp. [° C.] | Activity [kg(PK)$^{a)}$/g(Pd)/h] | Viscosity VZ$^{b)}$ [ml/g] |
|---|---|---|---|---|---|---|
| 1 | 0.009 | 5 | 80 | 80 | 0.542 | 170 |
| 2 | 0.017 | 5 | 80 | 60 | 0.366 | 667 |
| 3$^{c)}$ | 0.01 | 5 | 80 | 80 | 0.013 | n.d.$^{d)}$ |
| 4 | 0.01 | 1 | 60 | 90 | 0.761 | n.d.$^{d)}$ |

$^{a)}$PK = carbon monoxide/ethene copolymer
$^{b)}$Determined in a 0.5% strength by weight o-dichlorobenzene/phenol (1:1) solution with the aid of a capillary viscometer.
$^{c)}$Comparative Experiment 1: the catalyst used was [1,3-bis(diphenylphosphino)propane]palladium(II) acetate.
$^{d)}$n.d. = not determined Comparative Example 2

Ethene and carbon monoxide were copolymerized according to the above method in the presence of [Pd(dppp-SO$_3$Na) (acetate)$_2$] (0.01 mmol) and p-toluenesulfonic acid (0.1 mmol) for 3 hours at 80 bar and 90° C.

Catalyst activity: 0.038 kg of polymer/g of Pd/h

Comparative Example 3

Ethene and carbon monoxide were copolymerized according to the above method in the presence of [Pd(CH$_3$CN)$_2$(OTs)$_2$] (0.02 mmol), dppp-SO$_3$Na (0.02 mmol) and p-toluenesulfonic acid (0.02 mmol) for 1 hour at 80 bar and 90° C.

Catalyst activity: 0.226 kg of polymer/g of Pd/h
Viscosity number: 52 ml/g

No reproducible results could be obtained with the in situ catalyst system according to Comparative Example 3. The above catalyst activity represents a value at the upper limit. Frequently, however, only traces of copolymer were found.

We claim:

1. A process for the preparation of linear, alternating copolymers of carbon monoxide and α-olefinically unsaturated compounds, said process comprising preparing said copolymers in the presence of a water-soluble transition metal complex of the formula (I)

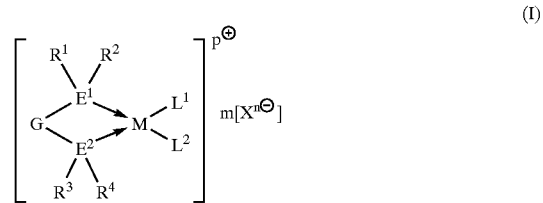

where
G is —(CR$^b{}_2$)$_r$—, —(CR$^b{}_2$)$_s$—Si(R$^a$)$_2$—(CR$^b{}_2$)$_t$—, —A'—O—B'— or —A'—Z(R$^5$)—B'— where
R$^5$ is hydrogen or is C$_1$- to C$_{28}$-alkyl, C$_3$- to C$_{14}$-cycloalkyl, C$_6$- to C$_{15}$-aryl or C$_7$- to C$_{35}$-alkylaryl where the alkyl radical is of 1 to 20 carbon atoms and the aryl radical is of 6 to carbon atoms, each of which is unsubstituted or substituted by functional groups based on elements of groups IVA, VA, VIA or VIIA of the Periodic Table of the Elements, or is —N(R$^b$)$_2$, —Si(R$^c$)$_3$ or a radical of the formula II

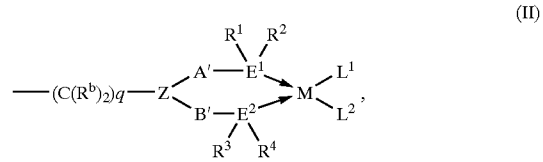

where
q is an integer from 0 to 20 and the further substituents in (II) have the same meanings as in (I),
A' and B' are each —(CR$^b{}_2$)$_r$—, or —(CR$^b{}_2$)$_s$—Si(R$^a$)$_2$—(CR$^b{}_2$)$_t$—,
R$^a$ independently of one another, are each C$_1$- to C$_{20}$-alkyl, C$_3$- to C$_{10}$-cycloalkyl, C$_6$- to C$_{15}$-aryl or C$_7$- to C$_{25}$-alkylaryl where the alkyl moiety is of 1 to 10 carbon atoms and the aryl moiety is of 6 to 15 carbon atoms,
R$^b$ is the same as R$^a$, or hydrogen or Si(R$^c$)$_3$,
R$^c$ is C$_1$- to C$_{20}$-alkyl, C$_3$- to C$_{10}$-cycloalkyl, C$_6$- to C$_{15}$-aryl or C$_7$- to C$_{25}$-alkylaryl where the alkyl moiety is of 1 to 10 carbon atoms and the aryl moiety is of 6 to 15 carbon atoms,
r is 1, 2, 3 or 4,
r' is 1 or 2,
s and t are each 0, 1 or 2, where 1≦s+t ≦3
Z is nitrogen, phosphorus, arsenic or antimony,
M is a metal selected from the groups VIIIB, IB or IIB of the Periodic Table of Elements,
E$^1$ and E$^2$ are each nitrogen, phosphorus, arsenic or antimony,
R$^1$ to R$^4$ are each linear or branched C$_2$ to C$_{28}$-alkyl, C$_3$ to C$_{14}$-cycloalkyl or C$_7$- to C$_{43}$-alkylaryl where the alkyl moiety is of 1 to 28 carbon atoms and the aryl moiety is of 6 to 15 carbon atoms, each of which is substituted by at least one polar protic or ionic functional group based on nonmetallic elements of groups IVA to VIA of the Periodic Table of Elements, $L^1$ and $L^2$ are formally charged or neutral ligands, X are formally monovalent or polyvalent anions, p is 0, 1, 2, 3 or 4, m and n are each 0, 1, 2, 3 or 4, where p=m×n.

2. The process of claim 1, wherein

G is —$(CR^b{}_2)_r$— or —$(CR^b{}_2)$—$N(R^5)$—$(CR^b{}_2)$—, where $R^b$ is hydrogen, $C_1$- to $C_{10}$-alkyl or $C_6$- to $C_{10}$-aryl, r is 1, 2, 3 or 4, $R^5$ is hydrogen, $C_1$- to $C_{10}$-alkyl, $C_3$- to $C_{10}$-cycloalkyl, $C_6$- to $C_{15}$-aryl or $C_1$- to $C_{10}$-alkyl, $C_3$- to $C_{10}$-cycloalkyl or $C_6$- to $C_{15}$-aryl, which is substituted by functional groups based on elements of groups IVA, VA, VIA and VIIA of the Periodic Table of Elements, M is palladium or nickel, $E^1$ and $E^2$ are each phosphorus, $R^1$ to $R^4$ are linear, branched or carbocycle-containing $C_2$- to $C_{28}$-alkyl units or $C_3$- to $C_{14}$-cycloalkyl units which have at least one terminal or internal hydroxyl, amino, carboxyl, phosphonyl, ammonium or sulfonyl group, or $C_7$–$C_{35}$-alkylaryl where the alkyl moiety is of 1 to 20 carbon atoms and the aryl moiety is of 6 to 15 carbon atoms, the alkyl or aryl moiety being substituted by at least one hydroxyl, carboxyl, amino, phosphonyl, sulfonyl or ammonium group, $L^1$ and $L^2$ are each acetate, trifluoroacetate, tosylate or halide, and p, m, n are each 0.

3. The process of claim 1, wherein $R^1$ to $R^4$ are linear, branched or carbocycle-containing $C_2$- to $C_{28}$-alkyl units or $C_3$- to $C_{14}$-cycloalkyl units which have at least one terminal or internal hydroxyl, amino, carboxyl, phosphonyl, ammonium or sulfonyl group, or are each alkylaryl where the alkyl moiety is of 1 to 28 carbon atoms and the aryl moiety is of 6 to 15 carbon atoms, the alkyl or aryl moiety being substituted by at least one hydroxyl, amino, carboxyl, phosphonyl, ammonium or sulfonyl group.

4. The process of claim 1, wherein $R^5$ is tert-butyl, phenyl, p-triflurophenyl, trifluoromethyl, 2,2,2-trifluoroethyl, pentafluorophenyl, 3,5-bis(trifluoromethyl)phenyl, ortho-difluorophenyl, meta-difluorophenyl or para-difluorophenyl.

* * * * *